United States Patent [19]

Tochacek et al.

[11] Patent Number: 4,770,917
[45] Date of Patent: Sep. 13, 1988

[54] SHEET MATERIAL USED TO FORM PORTIONS OF FASTENERS

[75] Inventors: Miroslav Tochacek, Woodbury; Paul E. Hansen, Lake Elmo, both of Minn.

[73] Assignee: Minnesota Mining and Manufacturing Company, Saint Paul, Minn.

[21] Appl. No.: 760,999

[22] Filed: Jul. 31, 1985

[51] Int. Cl.⁴ .................................................. B32B 3/02
[52] U.S. Cl. ........................................ 428/95; 156/72; 428/85; 428/92; 428/93; 428/94; 428/99; 428/100; 428/102; 428/296
[58] Field of Search ...................... 156/72; 428/85, 92, 428/93, 94, 95, 253, 224, 225, 99, 100, 296, 102

[56] References Cited

U.S. PATENT DOCUMENTS

| | | | |
|---|---|---|---|
| 3,009,235 | 11/1961 | Mestral | 28/78 |
| 4,024,003 | 5/1977 | Buhler | 156/148 |
| 4,290,832 | 9/1981 | Kalleberg | 156/72 |
| 4,454,183 | 6/1984 | Wollman | 428/92 |
| 4,609,581 | 9/1986 | Ott | 428/100 |
| 4,673,604 | 6/1987 | Frain et al. | 428/95 |

Primary Examiner—James J. Bell
Attorney, Agent, or Firm—Donald M. Sell; William L. Huebsch

[57] ABSTRACT

A method for forming a sheet material adapted to be cut into smaller pieces to form portions of a fastener. The method comprises providing a backing laminate comprising a layer of base material and a sealing layer of heat softenable polymeric material along a back surface of the base material; stitching a plurality of yarns through the base material to form loops projecting from a face surface of the base material and locking portions of the stitch adjacent the back face of the base material; and heating the polymeric material to adhere it to the locking portions of the stitches. The sheet material can then be used if loops are desired, or the loops can be cut to form hooks or heated to form headed projections on the sheet material.

24 Claims, 3 Drawing Sheets

SHEET MATERIAL USED TO FORM PORTIONS OF FASTENERS

TECHNICAL FIELD

The present invention relates to sheet materials that can be cut into smaller pieces to form portions of fasteners, and methods for forming such sheet materials.

BACKGROUND ART

The art is replete with various sheet materials that can be cut into smaller pieces to form portions of fasteners, and methods for making such sheet materials. U.S. Pat. Nos. 3,009,235; 4,024,003; 4,290,832; 4,454,183 provide illustrative examples. Generally these patents have described sheet materials including backings from which project yarns that form either loops, loops cut along one side to form hooks, or projections that have enlarged heads at their distal ends, and which backings anchor portions of the yarns so that the loops, hooks or headed projections on pieces of such material may be engaged with other such structures on pieces of other such sheet materials to form fasteners.

Such yarns have been either embedded into a polymeric backing layer while it was heat softened so that the yarns were fused to the backing; or woven into a cloth backing that was of regularly woven construction, which backing was then coated with an adhesive-like material applied by spraying, soaking or extruding so that the yarns were more solidly anchored in place. The former method provides extremely strong anchoring of the yarns by fusing them to the backing layer, however, it requires complex and expensive special equipment to make wide widths of the material. The latter method can be used to make materials in wide widths, however, it is slow and requires an extra step to apply the adhesive-like material to the backing so that the cost of the resultant sheet material is relatively high.

DISCLOSURE OF THE INVENTION

The present invention provides a method for forming a sheet material of the type described above which is adapted to be cut into smaller ravel resistant pieces to form portions of a fastener, which method affords both manufacturing the sheet material in wide widths on commercially available equipment using non-woven backing layers, and bonding the yarns onto the backing layer on the same production line on which the yarns are set into the backing.

The method according to the present invention for forming a sheet material adapted to be cut into smaller ravel resistant pieces to form portions of a fastener comprises the steps of (1) providing a backing laminate comprising a layer of base material and a sealing layer of heat softenable polymeric material along a back face of the base material; (2) stitching a plurality of yarns through at least the base material of the backing laminate to form loops projecting from a front face of the base material and locking portions of the stitches adjacent the back face of the base material; and (3) heating the polymeric material to adhere it to the locking portions of the stitches.

The yarns can be stitched through both the base material and the sealing layer, or the yarns can be stitched only through the base material whereupon the sealing layer is positioned along the back face of the base material over the locking portions of the stitches between the stitching and the heating steps.

Preferably the heating step also adheres the polymeric material to the base material, and the yarns are of a heat softenable polymeric material so that the heating step fuses the locking portions of the stitches together and to the softened polymeric material from the sealing layer which provides very firm anchoring of the yarns in the backing laminate.

In addition to anchoring the yarns in the backing laminate, the polymeric material from the sealing layer can also provide means for heat sealing pieces of the sheet material to a substrate by heating the pieces so that the polymeric material from the sealing layer softens and adheres to the substrate.

Also, preferably the stitching and heating steps are performed continuously during movement of the backing laminate along the same production line so that the sheet material can be rapidly and economically produced.

The method as described above may be used to form sheet material having projecting loops either by using monofilament yarns to provide maximum loop strength for a given yarn diameter, or by using multifilament yarns that, compared to monofilament yarns, can greatly increase the number of loops formed for a given number of stitches. Alternatively sheet material having a plurality of projecting hooks may be made by using monofilament yarns of a heat settable polymer (e.g., nylon or polyester) and adding the further steps of heating the loops so that they will resiliently retain their shape, and cutting each loop along one side to form the hooks; or sheet material having projections with enlarged heads on their distal ends may be made by using monofilament yarns to form the loops and the further step of heating the upper portions of the loops to melt their central portions and form from each loop two projections with enlarged heads on their distal ends. Such heads can be made mushroom or globular shaped by selecting the proper polymeric material for the yarns (e.g., polypropylene or nylon respectively) as is well known in the art, or can be caused to have hook-like portions projecting from the heads along the yarns that connect them to the backing by using monofilament yarns of polypropylene with lobes around their peripheries as is taught in U.S. Pat. No. 4,454,183 incorporated herein by reference.

At present the only known machines capable of stitching the yarns through the base material or backing laminate at commercially acceptable rates are the Malimo ™ type Malipol Stitch-Knitting Machine manufactured by Textima in East Germany and distributed in the United States by Chima, Inc. of Reading, Pennsylvania; and the Czechloslovak version ARACHNE Stitch bonding machine type Araloop, sold in the U.S. since 1966 through Stellamcor, Inc., New York and prior to 1979 by Omintex in Charlotte, N.C. It is believed, however, that new stitch knitting machines are presently under development by American Liba Corp. and Karl Mayer of West Germany that will also provide the needed stitching capability.

Such known stitch-knitting machines are available that can apply the stitches to base materials or backing laminates over 140 inches wide, can apply up to 1500 stitches per minute while applying about 12 stitches per inch (which is usable for forming sheet material according to the present invention), thereby producing stitched base material or backing laminate at a speed of about 625 feet per hour which is about 2 to 10 times greater than the speed at which similar looped structures could be produced by known weaving or knitting machines.

The loop height (i.e., the average height that the centers of the loops project above the base material) has been varied in the range of 1 to 5 millimeters on the stitch-knitting machine and loops so having heights in that range have been found to make acceptable engagement with hooks or headed stems on mating sheet material, or have been found to produce acceptable hooks or headed stems when further processed in accordance with the methods described above.

Preferably the loops are formed by making 14 to 18 longitudinal rows of stitches or wales per inch measured in a direction at a right angle to the wales, and making 10 to 40 stitches or courses per inch along each row or wale. It has been found that increasing the stitch density not only increases the number of anchoring sites for the stitches, but also causes the loops that are formed to stand more erect. Additionally it has been found that the loops can be made to stand more erect by forming stitches in the base material or backing laminate to help compress it at the base of the loops. This can be done by operating the stitch-knitting machine in a double bar mode in which two separate yarns are used for each stitch, one of which yarns forms the loop and the other of which yarns forms a stitch that compresses the base material or backing laminate at the base of the loop. Alternatively a novel approach has been developed in which the stitch-knitting machine is modified so that while it is operated in a single bar mode each yarn forms first a loop and then a stitch through the base material or backing laminate to compress it as will be explained in greater detail herein. This approach forms only half the number of loops normally formed in the base material or backing laminate by the conventional single or double guide bar modes, but compresses the base material or backing laminate at the base of the loops that are formed so that they stand quite erect, and does so with half the yarn that is required to obtain that same result by the double bar mode.

The main functions of the base material layer in the backing laminate are to provide body and durability for the backing laminate and to be sufficiently tough so that the base material can be stitched into without ripping or tearing. Preferably the base material is also relatively stiff and has a sufficient density to firmly anchor the stitches and provide support for the loops so that they will project outwardly from the front face of the base material. Base materials having a weight generally in the range of ½ to 5 ounces per square yard have been found to provide these functions.

The base material included in the backing laminate may include woven or knitted materials such as an open mesh scrim or cheesecloth which is inexpensive, dimensionally stable, and soft and light. Alternatively, and often preferably, the base material can consist of nonwoven materials because of their low cost relative to such woven or knitted materials. These nonwoven materials can include a reinforcing layer of strong polymeric filaments firmly bonded or fused together (e.g., CLAF No. 2001, cross laid polyethylene fibrillated film available from Conwed Corporation, St. Paul, Minnesota) to give the base material dimensional stability along its major surfaces, and a bulk layer of less expensive nonwoven natural or synthetic fibers (e.g., polyester, nylon, polypropylene, or rayon) that can add body to the backing layer, a preferred material being 4 ounce per square yard polypropylene web from Foss Company, Haverhill, Mass. When such a combination of reinforcing and bulk layers is used, it is preferable to place the reinforcing layer adjacent the layer of heat sealable polymeric material so that the heating step may at least partially fuse the heat sealable polymeric material to the reinforcing layer as well as to the locking portions of the stitches.

Alternatively, the bulk layer may include a foamed material such as an open or closed cell foam or may include solid layer materials such as of paper or polymers to provide a desired appearance or structural characteristic, all of which types of material are considered to be nonwoven for purposes of the disclosure and claims herein.

The purpose of the sealing layer of heat softenable material is to provide material that, when heated will flow around and bond to the locking portions of the stitches and preferably at least partially to the base material to anchor the yarns to the backing laminate. Suitable heat softenable polymeric materials for use in the sealing layer include polyalkylenes such as polyethylene, polypropylene and the like, polyesters having an ester linkage in the backbone chain such as polyethylene terephthalate, polyamides such as nylons, polyvinyl chloride, polysulfones, polystyrene and polyurethanes such as polyether polyurethanes. Copolymers of the monomers which provide the above polymers are also useful. Presently preferred materials are polyethylene, polypropylene, the copolymers of ethylene and acrylic acid, the copolymers of ethylene and propylene and the copolymers of ethylene and vinyl acetate. Film layers of these preferred materials in the thickness range of about 0.0013 to 0.05 centimeter (0.0005 to 0.02 inch) and preferably in the range of about 0.005 to 0.013 centimeter (0.002 to 0.005 inch) have been found to be useful, with the thicker layers being preferable when pieces of the sheet material are to be heat fused to a substrate.

BRIEF DESCRIPTION OF THE DRAWING

The present invention will be further described with reference to the accompanying drawing wherein like numbers refer to like parts in the several views, and wherein.

DETAILED DESCRIPTION OF THE DRAWING

Figure 1:
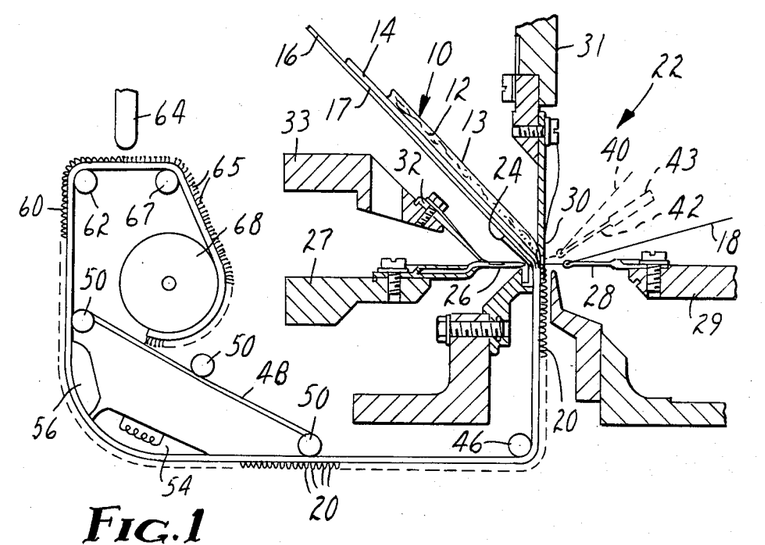
FIG. 1 schematically illustrates a method according to the present invention for making the stitched intermediate materials or sheet materials according to the present invention shown in FIGS. 2 through 11.

Referring now to FIG. 1 of the drawing, there is schematically illustrated a method according to the present invention for forming several sheet materials adapted to be cut into smaller pieces to form portions of a fastener.

Generally the method illustrated in FIG. 1 comprises the steps of providing a backing laminate 10 comprising a layer of base material which may as illustrated include a body layer 12 of woven or nonwoven, natural or synthetic fibers that provides a front face 13 for the base material and a reinforcing layer 14 of strong yarns attached together as by weaving, gluing or fusing to provide structural strength and dimensional stability along the backing laminate 10. Also included in the backing laminate 10 is a sealing layer 16 of heat softenable polymeric material disposed along a back face 17 of the base material with the sealing layer 16 adjacent the reinforcing layer 14. A plurality of yarns 18 are stitched through the entire backing laminate 10 to form portions of the yarns 18 into loops 20 projecting from the front face 13 of the base material and locking portions 21 of the stitch along the sealing layer 16 of polymeric material. Such stitching is accomplished by a stitch-knitting machine 22 (e.g., a Malimo ™ type Malipol Stitch-knitting Machine). The stitch-knitting machine 22 can be used in various ways, but as used in this invention comprises means including a guide 24 for guiding the backing laminate 10 from a downwardly sloping path portion to a vertical path portion, a row of horizontal evenly spaced parallel needles 26 fixed to a needle bar 27, which needles 26 have recesses spaced from their points, and are longitudinally reciprocated by the needle bar 27 to repeatedly pierce the backing laminate 10 at the junction between the sloping and vertical path portions as the backing laminate 10 is moved past that junction, a row of evenly spaced yarn guides 28 attached to a bar 29 positioned on the side of the path for the backing laminate 10 opposite the needles 26, which yarn guides 28 have openings in their distal ends through which the yarns 18 are guided and can locate the yarns 18 to engage them with the recesses in the needles 26 when the ends of the needles 26 have pierced the backing laminate 10, a row of vertically downwardly projecting loop sinkers 30 fixed to a support 31, around which loop sinkers 30 the loops 20 are formed, and a row of closing wires 32 fixed to a support 33, each of which wires 32 moves both with and relative to an associated needle 26 to cover and uncover the recess spaced from the point of that needle 26 at appropriate times in the operating cycle of the machine 22.

Generally, as used in the method according to the present invention, the stitch-knitting machine 22 is operated as a stitching machine so that repeatedly the row of horizontal needles 26 pierces the backing laminate 10 while passing between the loop sinkers 30 so that the points and recesses along the needles 26 move between and past the loop sinkers 30 to an extended position between the yarn guides 28, while the closing wires 32 move relative to the needles 26 to open the recesses in the needles 26 when the needles 26 arrive in that extended position. Simultaneously, the bar 29 moves the yarn guides 28 in a generally semicircular pattern around the ends of the needles 26 to lay yarns 18 guided through openings in the yarn guides 28 into the open recesses in the needles 26. The needles then are pulled back through the backing laminate 10 as the closing wires 32 again move relative to the needles 26 to close the recesses so that the needles 26 will pull the yarns 18 through the backing laminate 10. The backing laminate is advanced between repetitions of this cycle at a rate that determines the lengths of the stitches that are formed by subsequent piercing of the backing laminate 10 by the needles 26.

The machine 22 can be operated by using an appropriate cam in conjunction with the bar 29 so that in addition to moving the yarn guides 28 around the ends of the needles 26 to lay the yarns 18 in the recesses in the needles 26, the bar 29 will also move the yarn guides 28 back and forth between two adjacent needles 26 positioning each length of yarn 18 in one needle 26 the first time the needles pierce the backing laminate 10 and in the other needle 26 the next time the needles pierce the backing laminate 10. Thus the length of yarn 18 extends around the loop sinker 30 between those two adjacent needles 26 each time the yarn 18 is pulled through the backing laminate 10 to form the loops 20. When operated in this single bar mode the machine 22 will form a stitched intermediate material 36a illustrated in FIGS. 2, 3 and 4 comprising the backing laminate 10 including the layer of base material formed from the body and reinforcing layers 12 and 14, a plurality of rows of the yarn 18 stitched through the backing laminate 10 and having portions forming the loops 20 projecting from the front face of the layer of base material and the locking portions 21 locking the stitches adjacent the back face 17 of the base material and along the sealing layer 16 of polymeric material.

Figure 6:
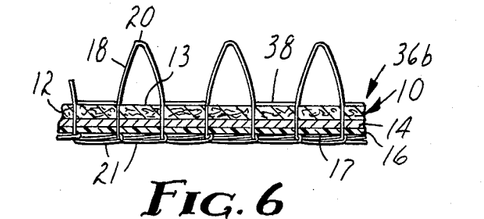
FIG. 6 is an enlarged edge view of a second stitched intermediate material that can be made during a portion of the method shown in FIG. 1.
Figure 7:
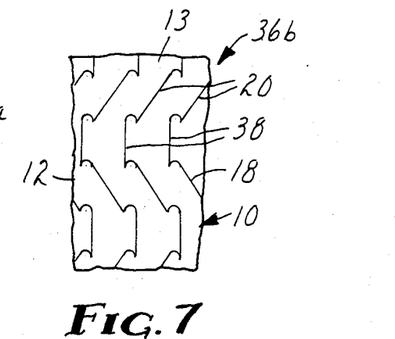
FIG. 7 is a fragmentary top view of the stitched intermediate material of FIG. 6.

Alternatively, the machine 22 can be operated by providing and using an appropriate cam in conjunction with the bar 29 so that in addition to moving the yarn guides 28 around the ends of the needles 26 to lay the yarn 18 in the recesses in the needles 26, the bar 29 will also move the yarn guides 28 between adjacent needles 26 after each second piercing of the backing laminate 10, thereby positioning each length of yarn 18 in the same first needle 26 the first two times the needles 26 pierce the backing laminate 10, and in an adjacent needle 26 the next two times the needles 26 pierce the backing laminate 10 as a completion of the pattern repeat which starts again by the yarn guides 28 placing the yarn 18 in the first needle 26 the next two times the needles pierce the backing laminate 10. Thus the length of yarn 18 extends around the loop sinker 30 between those adjacent needles 26 each second time the yarn 18 is pulled through the backing laminate 10. When operated in this single bar mode the machine 22 will form a stitched intermediate material 36b illustrated in FIGS. 6 and 7 comprising the backing laminate 10 including the layer of base material formed from the body and reinforcing layers 12 and 14, a plurality of rows of the yarn 18 stitched through the backing laminate 10 and having portions forming loops 20 projecting from the front face of the layer of base material, a tightening portion 38 along the front face 13 of the backing laminate 10 between each loop 20 that pulls the backing laminate 10 together, and locking portions that are the same as the locking portions 21 shown in FIG. 4 locking the stitches adjacent the back face 17 of the base material and along the sealing layer 16 of polymeric material.

Figure 2:
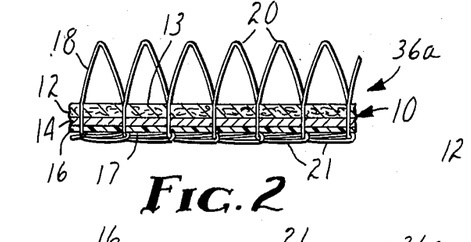
FIG. 2 is an enlarged edge view of a first stitched intermediate material that can be made during a portion of the method shown in FIG. 1.
Figure 3:
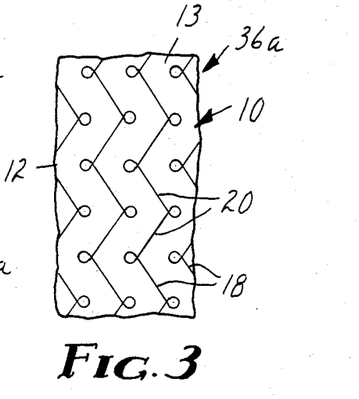
FIG. 3 is a fragmentary top view of the stitched intermediate material of FIG. 2.
Figure 4:
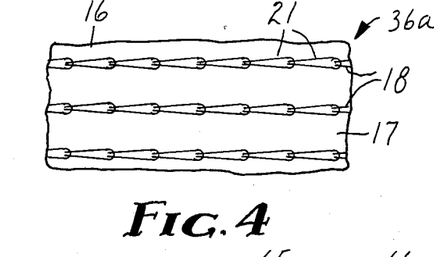
FIG. 4 is a fragmentary bottom view of the stitched intermediate material of FIG. 2.

Also, the machine 22 can be operated in the manner described above to make the intermediate material 36a illustrated in FIGS. 2, 3 and 4, and modified so that each needle also sews a second yarn 40 into the backing laminate 10 by using a second set of yarn guides 42 attached to a bar 43 (shown in dotted outline in FIG. 1) to guide the yarns 40. A cam used in conjunction with the bar 43 continuously moves each of the second yarn guides 42 around the end of the same needle 26 to lay the second lengths of yarn 40 in the recesses in that needle 26 when it is in its extended position so that the second lengths of yarn 40 are never positioned around the loop sinkers 30 between two adjacent needles 26. When operated in this double bar mode the machine 22 will form a stitched intermediate material 36c illustrated in FIGS. 9 and 10 comprising the backing laminate 10 including the layer of base material formed from the body and reinforcing layers 12 and 14, a plurality of rows of the yarn 18 stitched through the backing laminate 10 and having portions forming the loops 20 projecting from the front face 13 of the layer of base material and locking portions 21 locking the stitches along the back face 17 of the base material and the sealing layer 16 of polymeric material, and a plurality of corresponding rows of the second yarns 40 stitched through the backing laminate 10 and having tightening portions 44 at the base of each loop 20 laying along the front face 13 of the backing laminate 10, and locking portions 21 locking the stitches adjacent the back face 17 of the base material and along the sealing layer 16 of polymeric material.

Figures 9, 10, 11:
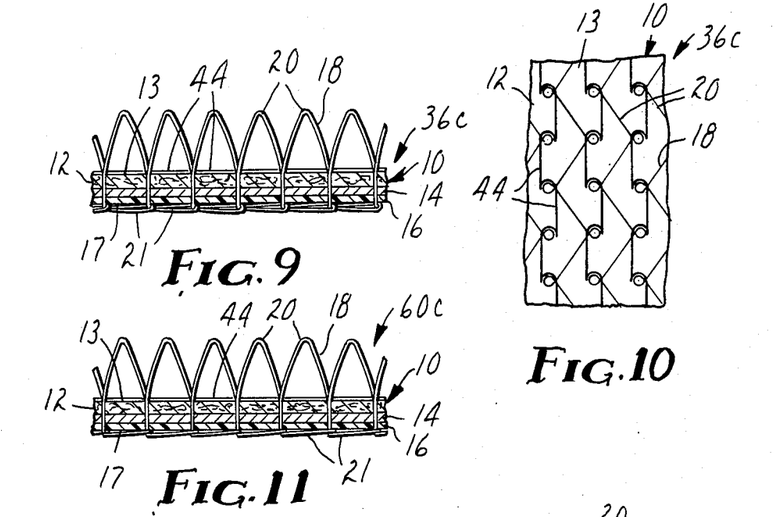
FIG. 9 is an enlarged edge view of a third stitched intermediate material that can be made during a portion of the method shown in FIG. 1.
FIG. 10 is a fragmentary top view of the stitched intermediate material of FIG. 9.
FIG. 11 is an enlarged edge view of a sheet material having projecting loops that can be made by a portion of the method shown in FIG. 1.

Subsequent to the loops 20 being formed by the machine 22, the stitched intermediate 36 (a, b or c) moves around a take-off roller 46 (FIG. 1) and then onto the surface of an endless metal belt 48 extending around three guide rollers 50, and along a heated shoe 54 and a cooling shoe 56, which belt 48 is driven in synchronism with the stitched intermediate 36 by a drive mechanism (not shown). As it passes over the heated shoe 54 and the cooling shoe 56, the belt 48 is first heated to a surface temperature (e.g., 245° C.) sufficient to soften the layer of polymeric material 16 and adhere it to the backing laminate 10 and the locking portions 21 of the stitches, and is then cooled to allow the polymeric material of the sealing layer 16 to separate from the belt 48. If the yarns 18 (and 40 if present) are of a heat softenable polymeric material, such heating by the shoe 54 through the belt 48 heats the locking portions 21 of the stitches to fuse them both to each other and to the softened polymeric material from the sealing layer 16 as is illustrated in FIG. 11.

Thus in the method illustrated in FIG. 1, the stitching and heating steps are performed continously during movement of the backing laminate 10 along the same production line through the stitch-knitting machine 22 and around the heated belt 48 to form sheet materials 60a, 60b, or 60c corresponding to the stitched intermediates 36a, 36b. and 36c respectively (of which only sheet material 60c is shown, see FIG. 11), which sheet materials 60 (a, b or c) have projecting loops 20 and are adapted to be cut into smaller pieces to form portions of fasteners.

Figure 5:
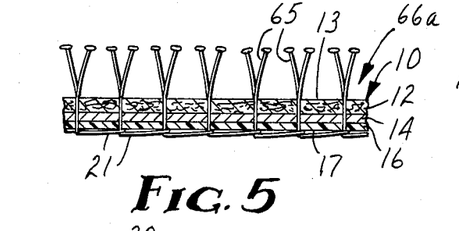
FIG. 5 is an enlarged edge view of a first headed sheet material that can be made by the method shown in FIG. 1.
Figure 8:
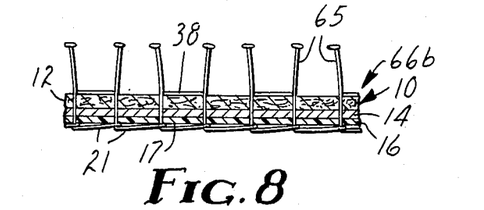
FIG. 8 is an enlarged edge view of a second headed sheet material that can be made by the method shown in FIG. 1.

As an alternative to using the sheet material 60 in the form that it leaves the belt 48, the sheet material 60 (a, b or c) can be passed around an idle roller 62 and further processed on the same production line illustrated in FIG. 1 by passing the loops 20 under a heat source illustrated as a heated wire 64, but which could be other forms of heaters. The heated wire 64 causes the centers of the loops 20 to melt and form from each loop 20 two headed stems 65 as is illustrated in FIGS. 5 and 8 which show sheet materials 66a and 66b respectively produced from the stitched intermediates 36a and 36b respectively, it being understood that a similar sheet material 66c could be made from the sheet material 36c.

From the hot wire 64 the completed sheet material 66 (a, b or c) can be passed around a guide roller 67 and wound into a supply roll 68 from which smaller pieces may be cut to provide parts of fasteners.

Figure 12:
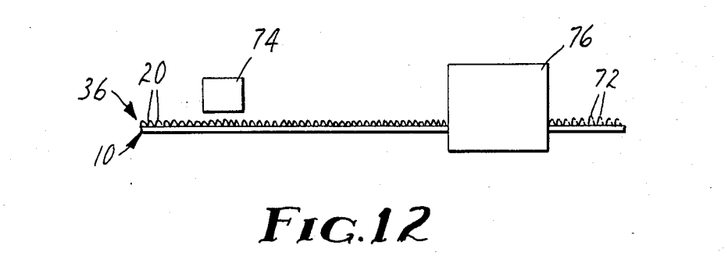
FIG. 12 schematically illustrates a method for further processing the sheet material of FIG. 11.
Figure 13:
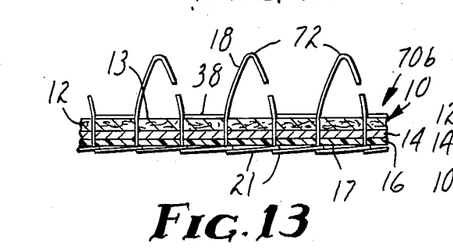
FIG. 13 is an enlarged edge view of a sheet material with projecting hooks made using the methods shown in FIGS. 1 and 12.

As an alternative to making the sheet materials 36 (a, b or c) with their projecting loops 20, or making sheet materials 66 (a, b or c) with headed stems 65 as described above, the method may also be used to form sheet materials 70 (a, b or c) with projecting hooks 72 as illustrated by sheet material 70b in FIG. 13 by further processing the sheet material 36 (a, b or c) as shown in FIG. 12. As illustrated in FIG. 12, the loops 20 of an appropriate yarn (e.g., nylon or polyester monofilament) may be heat treated as by a heat source 74 to cause them to resiliently retain their loop like shape, and may then be passed through a hook cutting device 76 (e.g., Loop Cutting Machine, Type PSM, made by Jacob Muller, Frick, Switzerland) to cut each loop along one side and form the hooks 72 on the sheet material 70 (a, b or c).

Figure 14:
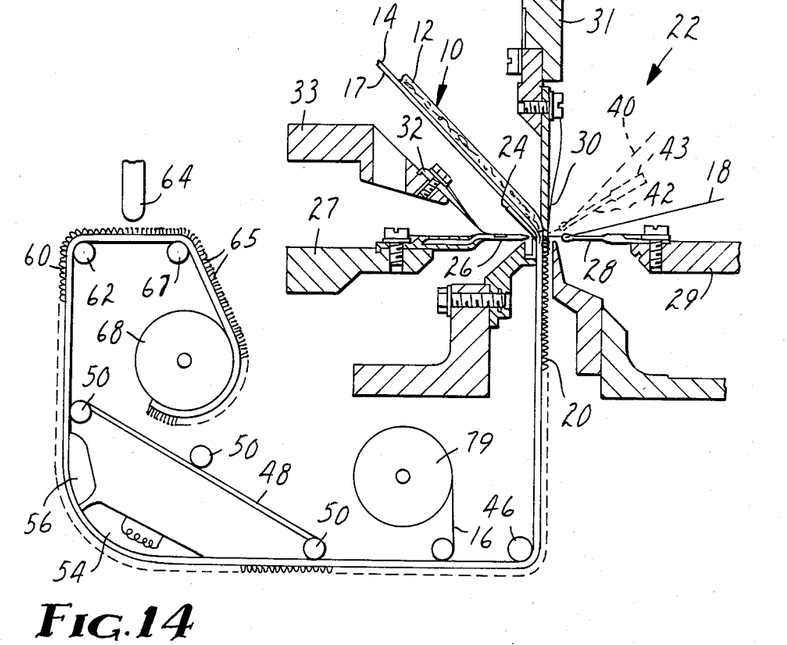
FIG. 14 schematically illustrates an alternative method according to the present invention for making stitched intermediate materials and sheet materials according to the present invention similar to those shown in FIGS. 2 through 11.
Figure 15:
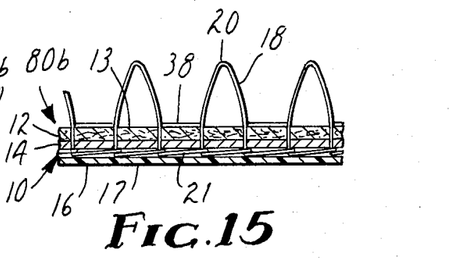
FIG. 15 is an enlarged edge view of a stitched intermediate material that can be made during a portion of the method shown in FIG. 14.

FIG. 14 illustrates an alternate method according to the present invention for forming several sheet materials adapted to be cut into smaller pieces to form portions of fasteners using the stitch-knitting machine 22 with the guide 24 for guiding the backing laminate 10, the needles 26, the yarn guides 28 attached to the bar 29 (and the yarn guides 42 attached to the bar 43 if needed), the loop sinkers 30, and the closing wires 32, which machine 22 may be operated in any of the modes described above to form the various patterns of loops and stitches; the endless metal belt 48, and the rollers 50, heated shoe 54 and cooling shoe 56 around which it extends; and the heated wire 64 (if needed). In the method illustrated in FIG. 14, unlike that illustrated in FIG. 1, however, only the layer of base material including the body layer 12 and the reinforcing layer 14 is passed through the machine 22 so that the yarns 18 are only stitched through the base material; and the sealing layer 16 of heat softenable polymeric material is then fed from a supply roll 79 along the back face 17 of the base material with the sealing layer 16 adjacent the reinforcing layer 14 over the locking portions 21 of the stitches to form an intermediate material 80b illustrated in FIG. 14 which is comparable to the intermediate material 36b described above. When the intermediate material 80b is further processed by being passed over the heated and cooled belt 48, the resultant sheet material 36b (FIG. 11) produced will be essentially identical to the sheet materials produced by the method illustrated in FIG. 1 in that the layer of polymeric material 16 is adhered to the backing laminate 10 and to the locking portions 21 of the stitches, and if the yarns 18 (and 40 if present) are of a heat softenable polymeric material, the locking portions 21 of the stitches may be fused both to each other to the softened polymeric material from the sealing layer 16.

EXAMPLE 1

The stitched intermediate 36a shown in FIG. 1 was made using a Malimo TM 14012 stitch-knitting machine having 14 gauge needles 26, 3 millimeter high loop sinkers 30, and set to produce 5.5 vertical rows of stitches per centimeter of width (14 rows of stitches per inch of width) and 5.1 stitches per centimeter (13 stitches per inch) along each vertical row so that about 28 loops per square centimeter (182 loops per square inch) were formed. The backing laminate used included a body layer 12 of 171 gram per square meter (5 ounce per square yard) 6 denier polypropylene fibers (6.36 centimeter staple) which had been mechanically felted on a needle loom with about 157 punches per square centimeter, and a reinforcing layer 14 of polyethylene nonwoven scrim weighing 51 grams per square meter (1.5 oz. per square yard) which is commercially designated CLAF and sold by Conwed Corporation, Saint Paul, Minn. The sealing layer 16 of polymeric material used was a 0.005 centimeter (0.002 inch) thick layer of ethylene-vinyl acetate film commercially designated VA24 and sold by Consolidated Thermoplastic, Chippewa Falls, Wis.; and the yarn 18 used was 236 denier polypropylene monofilament from Ametek Incorporated, Odenton, Md.

After the stitched intermediate 36a was formed, it was heat sealed by positioning its surface opposite the loops 20 on one surface of a steel belt and sliding the opposite surface of the belt across a plate heated to a surface temperature of 288° C. (550° F.) after which the belt was allowed to cool and the sheet material 60a was removed. This heat sealing caused the sealing layer 16, the locking portions 21 of the stitches and portions of the reinforcing layer 14 to melt and fuse together, providing firm anchoring for the loops 20.

Some of the sheet material 60a thus formed was slit to a more narrow width, and headed by passing it under a wire heated to a surface temperature of 538° C. (1000° F.) which was spaced from the loops 20 on the sheet material so that the centers of the loops were melted and each loop formed two stems with mushroom shaped heads on their distal ends to provide sheet material 66a having the structure described with reference to and shown in FIG. 5.

The sheet material 66a was light, flexible and soft and had sufficient projecting headed stems 65 to make secure releasable engagement with the loop portion of the product commercially designated Style 1719 tricot knit loop from Gehring Textiles, New York, N.Y. when forces were applied in shear, peel or tensile to separate them The sealing layers 16 on pieces of the sheet material 66a made by this example were heated to their melting point on a hot iron and pressed against the similarly heated polyethylene outer layer of a baby diaper sold under the trademark "Pampers." Upon cooling a firm bond was formed, and the heads on the pieces of sheet material provided firm engagement with material with projecting loops of the type commercially designated Style 997371 Millilock, available from Milliken and Company, New York, N.Y.

EXAMPLE 2

The stitched intermediate 36b (FIG. 6) was made using the same machine 22, needles 26, loop sinkers 30, stitch spacing and length settings, and materials described in Example 1. The sealing layer 16, stitch locking portion 21 and portions of the reinforcing layer 14 were also fused using the heat sealing procedure described in Example 1. The resultant sheet material 60b was light, flexible and soft like the sheet material 60a produced in Example 1, was judged to be more durable than the sheet material 60a because of the reinforcing provided by the tightening portions 38 of the stitches, but had only one half the loops 20 per given area compared to the sheet material 60a of FIG. 1. Those loops 20 stood more erect than the loops 20 formed in Example 1, however, and had more of their inner openings exposed due to compression of the backing laminate 10 by the tightening portions 38 of the stitches. Some of the sheet material 60b was also headed by passing it under a heated wire as described in Example 1 to provide the sheet material 66b described with reference to and shown in FIG. 8. While sheet material 66b had only half as many headed stems 65 as the sheet material 66a described in Example 1, it still made reasonably secure releasable engagement with the loop portion of the product commercially designated Stype 1719 tricot knit loop available from Gehring Textiles, New York, N.Y., when forces were applied in shear, peal, or tensile to separate them.

EXAMPLE 3

The stitched intermediate materials 36a and 36b were made using the same machine 22, needles 26, loop sinkers 30, machine settings and materials described in Examples 1 and 2 except that the reinforcing layer 14 was changed to a lightweight woven scrim or cheesecloth of cotton yarns having a density of 14/10 and a weight of 50 grams per square meter (1.5 ounce per square yard), and the sealing layer 16 was changed to a 0.013 centimeter (0.005 inch) thick layer of polyethylene acrylic acid copolymer sold commercially as No. 899 Dow Adhesive Film by Dow Corning, Inc., Midland, Mich. The same heat sealing procedure described in Example 1 was used to form sheet materials 60a and 60b with projecting loops 20, and a portion of those sheet materials 60a and 60b were headed as described in Example 1. The sheet materials 60a, 60b, 66a and 66b made with these materials were generally comparable to those produced in Examples 1 and 2 except that they were slightly less flexible and because of their thicker sealing layers 16 could be heat sealed more firmly to a metal surface which might be advantageous for fasteners used for various purposes such as in automobiles.

EXAMPLE 4

The stitched intermediate material 36c was made using the same machine 22, needles 26, loop sinkers 30, machine settings and materials described in Examples 1 and 3 except that the machine 22 was operated in its double bar mode utilizing both the yarn guides 28 on the bar 29 and the yarn guides 42 on the bar 43, with second 90 denier polyester yarns 40 being applied through the yarn guides 42 to form the stitches having tightening portions 44 at the bases of the loops 20. The same heat sealing procedure described in Example 1 was used to form sheet materials 60c with projecting loops 20 from the intermediate materials 36c, and a portion of those sheet materials 60c were headed as described in Example 1. The resultant sheet material 60c had the same number of loops 20 per given area as the sheet material 60a produced in Example 1, however, those loops 20 stood more erect than the loops 20 formed in Example 1 and had more of their inner openings exposed due to compression of the backing laminate 10 by the tightening portions 44 of the stitches. The headed sheet material 66c had as many headed stems 65 as the sheet material 66a described in Example 1 and was judged to be substantially more durable for use when many openings and closings of a fastener are anticipated.

EXAMPLE 5

The stitched intermediate materials 36a, 36b and 36c were made using the same machine 22, needles 26, loop sinkers 30, machine settings, materials, heat sealing procedure and heading procedure described in Examples 1 through 4 except that the sealing layer 16 was changed to a 0.013 centimeter (0.005 inch) thick layer of polyethylene acrylic acid copolymer sold commercially as No. 899 Dow Adhesive Film by Dow Corning, Inc., Midland, Mich. The sheet materials 60a, 60b, 60c, 66a, 66b and 66c made with these materials were generally comparable to those produced in Examples 1 through 4 except that they were more easily heat sealable to other surfaces and adhered more securely to those surfaces.

EXAMPLE 6

The stitched intermediate materials 36a, 36b and 36c were made using the same machine 22, needles 26, loop sinkers 30, machine settings, materials, heat sealing procedure and heading procedure described in Examples 1 through 4 except that the sealing layer 16 was changed to a 0.05 centimeter (0.02 inch) thick layer of polyethylene acrylic acid copolymer sold commercially as No. 899 Dow Adhesive Film by Dow Corning, Inc., Midland, Mich. The sheet materials 60a, 60b, 60c, 66a, 66b and 66c made with these materials were generally comparable to those produced in Examples 1 through 4 except that it was much more rigid. Also, these sheet materials were more easily heat bonded to an appropriate substrate by reheating the sealing layer 16.

EXAMPLE 7

Sheet materials 66a, 66b and 66c were made using the same machine 22, needles 26, loop sinkers 30, machine settings, materials, back sealing procedure and heading procedure described in Examples 1 through 4 except that the yarn 18 was changed to a polypropylene monofilament having about the same cross sectional area as the 236 denier monofilament, but having a generally triangular cross section. The sheet materials 60a, 60b, 60c, 66a, 66b and 66c made in this Example were generally comparable to those produced in Examples 1 through 4 except that the heads on those having headed stems 65 had hook-like portions projecting along their supporting stem toward the backing laminate as is described in U.S. Pat. No. 4,454,183, and thus developed much greater holding power, particularly in peel and tension, when the sheet materials made in this Example were engaged with fastener portions with projecting loops.

EXAMPLE 8

Sheet materials 60a, 60b and 60c were made using the same machine 22, needles 26, loop sinkers 30, machine settings, material and back sealing procedure described in Examples 1 through 4 except that the yarn 18 was changed to a texturized 200/10 denier nylon multifilament yarn. The projecting loops 20 on the sheet material 60a, 60b and 60c made in this example were generally comparable to those produced in Examples 1 through 4 except that many more loops 20 were present for potential engagement with mating fastener parts such as were made in Examples 1 through 7.

We claim:

1. A method for forming a sheet material adapted to be cut into smaller ravel resistant pieces to form portions of a fastener, said method comprising the steps of:
   providing a backing laminate comprising a layer of base material having a front face and a back face and a sealing layer of heat softenable polymeric material along the back face of the base material;
   stitching a plurality of yarns through the base material and the sealing layer of the backing laminate to form loops projecting from the front face of the base material and locking portions of the stitches adjacent the sealing layer of heat softenable polymeric material;
   heating the polymeric material after said stitching step to adhere the heat softenable polymeric material to the locking portions of the stitches.

2. A method according to claim 1 wherein the yarns are of a heat softenable polymeric material and said heating step includes heating the locking portions of the stitches to fuse them together and to the softened polymeric material of the sealing layer.

3. A method according to claim 1 wherein said stitching and heating steps are performed continuously during movement of the backing laminate along the same production line.

4. A method according to claim 1 wherein said step of stitching includes the step of forming parallel rows of stitch locking portions and along each of the rows the alternating sequence of only a chain locking stitch gathering the backing layer together within the locking stitch, and stitch forming a loop extending from the row of stitch locking portions to an adjacent row of stitch locking portions.

5. A method according to claim 1 wherein said method further includes the step of heating the upper portions of the loops to form from each loop two projections with enlarged heads on their distal ends.

6. A method according to claim 1 further including the steps of heating the loops to cause them to resiliently retain their shapes, and cutting the loops along one side to form hooks.

7. A method according to claim 1 wherein the heating step adheres the polymeric material to the base material.

8. A sheet material adapted to be cut into smaller ravel resistant pieces to form portions of fasteners, which sheet material is made by the method of claim 1.

9. A method for forming a sheet material adapted to be cut into smaller ravel resistant pieces to form portions of a fastener, said method comprising the steps of:
   providing a backing laminate comprising a layer of base material having a front face and a back face and a sealing layer of heat softenable polymeric material;

stitching a plurality of yarns through the base material to form loops projecting from the front face of the base material and locking portions of the stitches adjacent the back face of the base material;

positioning the sealing layer of heat softenable polymeric material along the back face of the base material over the locking portions of the stitches; and heating the polymeric material after said positioning step to adhere the heat softenable polymeric material to the locking portions of the stitches.

10. A method according to claim 9 wherein the yarns are of a heat softenable polymeric material and said heating step includes heating the locking portions of the stitches to fuse them together and to the softened polymeric material of the sealing layer.

11. A method according to claim 9 wherein said stitching and heating steps are preformed continuously during movement of the backing laminate along the same production line.

12. A method according to claim 9 wherein said step of stitching includes the step of forming parallel rows of stitch locking portions and along each of the rows the alternating sequence of only a chain locking stitch gathering the backing layer together within the locking stitch, and a stitch forming a loop extending from the row of stitch locking portions to an adjacent row of stitch locking portions.

13. A method according to claim 9 wherein said method further includes the step of heating the upper portions of the loops to form from each loop two projections with enlarged heads on their distal ends.

14. A method according to claim 9 further including the steps of heating the loops to cause them to resiliently retain their shapes, and cutting the loops along one side to form hooks.

15. A method according to claim 9 wherein said heating step adheres the polymeric material to the base material.

16. A sheet material adapted to be cut into smaller ravel resistant pieces to form portions of fasteners, which sheet material is made by the method of claim 9.

17. A sheet material adapted to be cut into smaller ravel resistant pieces to form portions of a fastener, said sheet material comprising: a backing laminate comprising a layer of base material having a front face and a back face; a plurality of heat softenable polymeric yarns stitched through the backing laminate and having portions projecting from the front face of said layer of base material and locking portions of the stitches adjacent the back face of the base material, said stitches forming parallel rows of stitch locking portions with each of said rows having the alternating sequence of only a chain locking stitch gathering the backing layer together within the locking stitch, and a stitch forming a loop extending from the row to an adjacent row; and a layer of polymeric material adhered to the layer of nonwoven material and to the locking portions of the stitches, said layer of polymeric material being heat softenable and sufficiently thick to afford attaching the sheet material to a substrate.

18. A sheet material according to claim 17 wherein said projecting portions have enlarged heads at their distal ends.

19. A sheet material according to claim 17 wherein said projecting portions form loops.

20. A sheet material according to claim 17 wherein said projecting portions are resiliently flexible hooks.

21. In combination, a substrate having a heat softenable polymeric surface, and a piece of a sheet material forming a portion of a fastner, comprising:

a backing laminate comprising a layer of base material having a front face and a back face;

a plurality of heat softenable polymeric yarns stitched through the backing laminate and having portions projecting from the front face of said layer of base material and locking portions of the stitches adjacent the back face of the base material, said stitches forming parallel rows of stitch locking portions with each of said rows having a the alternating sequence fo only a chain locking stitch gathering the backing layer together within the locking stitch, and a stitch forming a loop extending from the row to an adjacent row; and a layer of polymeric material adhered to the layer of nonwoven material and to the locking portions of the stitches, said layer of polymeric material adhering the layer of nonwoven material to the surface of the substrate.

22. A combination according to claim 21 wherein said projecting portions have enlarged heads at their distal ends.

23. A combination according to claim 21 wherein said projecting portions form loops.

24. A combination according to claim 21 wherein said projecting portions are resiliently flexible hooks.

* * * * *